United States Patent
Tretjak et al.

(10) Patent No.: US 10,647,657 B2
(45) Date of Patent: May 12, 2020

(54) PURIFICATION OF (METH)ACRYLIC ESTERS BY MEMBRANE SEPARATION DEHYDRATION

(71) Applicant: Arkema France, Colombes (FR)

(72) Inventors: Serge Tretjak, Roulhing (FR); Anne Moreliere, Longeville-les-St-Avold (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 15/102,921

(22) PCT Filed: Dec. 9, 2014

(86) PCT No.: PCT/FR2014/053223
§ 371 (c)(1),
(2) Date: Jun. 9, 2016

(87) PCT Pub. No.: WO2015/086978
PCT Pub. Date: Jun. 18, 2015

(65) Prior Publication Data
US 2016/0376217 A1    Dec. 29, 2016

(30) Foreign Application Priority Data
Dec. 13, 2013    (FR) ...................................... 13.62560

(51) Int. Cl.
*C07C 67/56*    (2006.01)
*B01D 61/36*    (2006.01)
(Continued)

(52) U.S. Cl.
CPC .............. *C07C 67/56* (2013.01); *B01D 3/145* (2013.01); *B01D 61/362* (2013.01);
(Continued)

(58) Field of Classification Search
None
See application file for complete search history.

(56) References Cited

U.S. PATENT DOCUMENTS

| | | | |
|---|---|---|---|
| 5,463,121 A | * | 10/1995 | Sridhar ................ B01D 61/362 562/600 |
| 6,755,975 B2 | * | 6/2004 | Vane .................... B01D 61/362 203/12 |

(Continued)

FOREIGN PATENT DOCUMENTS

| | | |
|---|---|---|
| FR | 2980475 A1 | 3/2013 |
| GB | 770 551 | 3/1957 |
| JP | 2002047213 A2 | 2/2002 |

OTHER PUBLICATIONS

Machine generated English language translation of FR 2980475, published on Mar. 29, 2013, p. 1-16.*

(Continued)

*Primary Examiner* — Amy C Bonaparte
(74) *Attorney, Agent, or Firm* — Lynn B. Morreale

(57) ABSTRACT

The invention relates to a method for producing alkyl (meth)acrylate comprising a linear or branched alkyl chain comprising 4 to 10 carbon atoms, by direct esterification of (meth)acrylic acid with a linear or branched alcohol comprising 4 to 10 carbon atoms in the presence of a catalyst, leading to formation of a reaction mixture comprising the desired ester, unreacted acid and alcohol, light by-products, and heavy by-products. The mixture undergoes purification treatment by separation means to obtain purified alkyl (meth)acrylate. The purification treatment comprises a step of membrane separation dehydration applied to at least one of the following: the stream subjected to the final distillation leading to the recovery of the purified (meth)acrylic ester, the aqueous stream originating from the settling out of the (Continued)

reaction mixture, or the stream resulting from the distillation of the light by-products present in the reaction mixture.

4 Claims, 3 Drawing Sheets

(51) Int. Cl.
    *C07C 67/08*     (2006.01)
    *B01D 71/02*     (2006.01)
    *B01D 71/38*     (2006.01)
    *B01D 3/14*     (2006.01)

(52) U.S. Cl.
    CPC ........... *B01D 71/028* (2013.01); *B01D 71/38* (2013.01); *C07C 67/08* (2013.01); *B01D 2311/2669* (2013.01); *Y02P 20/582* (2015.11)

(56) References Cited

U.S. PATENT DOCUMENTS

| | | | |
|---|---|---|---|
| 2006/0094895 A1* | 5/2006 | Patterson | C07B 41/12 560/231 |
| 2006/0211880 A1 | 9/2006 | Ackerman et al. | |
| 2008/0216649 A1* | 9/2008 | Huang | B01D 53/228 95/50 |
| 2009/0057224 A1* | 3/2009 | Huang | B01D 53/268 210/640 |
| 2013/0131397 A1* | 5/2013 | Warner | C07C 29/149 568/885 |

OTHER PUBLICATIONS

Truong ("Dehydration of reactive industrial mixtures by pervaporation: An innovative approach in acrylic esters processes" Separation and Purification Technology, 120, 2013, p. 24-34) (Year: 2013).*

* cited by examiner

PURIFICATION OF (METH)ACRYLIC ESTERS BY MEMBRANE SEPARATION DEHYDRATION

CROSS-REFERENCE TO RELATED APPLICATIONS

This application is a national stage application under 35 U.S.C. § 371 of PCT/FR2014/053223, filed Dec. 9, 2014, which claims benefit to application FR13.62560, filed Dec. 13, 2013.

FIELD OF THE INVENTION

The present invention relates to the production of (meth) acrylic esters, and its subject is more particularly an improvement in the production of $C_4$-$C_{10}$ alkyl (meth) acrylates, consisting in carrying out a step of membrane separation dehydration of at least one stream generated during the purification of said alkyl (meth)acrylate.

TECHNICAL BACKGROUND

It is known practice to produce (meth)acrylic esters from an esterification reaction between an alcohol and a (meth) acrylic acid. This reaction is an equilibrated catalyzed reaction with generation of water. It is also accompanied by side reactions producing impurities.

It is necessary to eliminate the water produced in order to shift the equilibrium, and it is necessary to recycle unreacted reagents (alcohol and acid) and also to eliminate impurities, in particular lighter compounds than the ester and heavier compounds than the ester, so as to obtain a product which meets commercial specifications.

To this end, a set of treatments of the reaction mixture is generally carried out, by means of distillations and/or extractions, or settling out operations, which set of treatments is both relatively complex to carry out, especially due to the presence of azeotropic mixtures, and costly in terms of energy.

The reaction mixture contains the desired ester, water, unreacted acid and alcohol, "light" by-products having a boiling point lower than that of the ester, and "heavy" by-products, that is to say having a boiling point higher than that of the ester. The purification sequence applied to the reaction mixture generates various streams, the composition of which varies depending on the apolar nature of the alcohol and of the ester, that is to say according to the length of the alkyl chain of the alcohol used. These streams share the common feature of containing water resulting from the reaction and/or the extraction steps.

In the process for producing (meth)acrylic ester described in patent application FR 2 980 475 in the applicant's name, modules for membrane separation dehydration are used to dehydrate streams comprising (meth)acrylic ester and unreacted alcohol with a view to effectively eliminating water and to produce good selectivity for (meth)acrylic ester. These modules are especially applied at the reaction step or at the unreacted alcohol recycling for a well-defined range of concentrations of the various compounds, and mainly in the case of producing $C_1$-$C_4$ alkyl (meth)acrylates such as methyl acrylate, ethyl acrylate or butyl acrylate.

Surprisingly, the applicant has now observed that, in the case of producing $C_4$-$C_{10}$ alkyl (meth)acrylates, it is possible to apply a step of membrane separation dehydration to aqueous streams outside the concentration ranges described in document FR 2 980 475. This leads to the effective elimination of the water present in the streams intended to be purified and/or recycled, which are separate from the treated aqueous streams in the process of the abovementioned document, and thus avoids the formation of a loop of water which is harmful to the productivity and energy consumption of the process. In particular, the dehydration step is advantageously applied upstream of the finishing column for the desired ester, or at the top of the column for separating the light compounds, or on the aqueous phase after settling out of the crude reaction mixture.

SUMMARY OF THE INVENTION

Thus, the subject of the invention is a process for producing an alkyl (meth)acrylate comprising a linear or branched alkyl chain comprising from 4 to 10 carbon atoms, by direct esterification of (meth)acrylic acid with a linear or branched alcohol comprising from 4 to 10 carbon atoms in the presence of a catalyst, leading to the formation of a reaction mixture comprising the desired ester, the unreacted acid and alcohol, light by-products and heavy by-products, which mixture undergoes a treatment for purification by separation means, in order to obtain the purified alkyl (meth)acrylate, said purification treatment being characterized in that it comprises a step of membrane separation dehydration applied to at least one of the following streams: the stream subjected to the final distillation leading to the recovery of the purified (meth)acrylic ester, the aqueous stream originating from the settling out of the reaction mixture, or the stream resulting from the distillation of the light by-products present in the reaction mixture.

According to one embodiment, the membrane separation dehydration is a dehydration by pervaporation or by vapor permeation.

According to one embodiment, the membrane separation is a separation on an inorganic membrane, preferably zeolite, and more particularly preferably T-type zeolite; or on a hydrophilic polymeric membrane, preferably a hydrophilic membrane based on polyvinyl alcohol.

According to one embodiment, the membrane separation is a separation on a hydrophobic polymeric membrane such as the 4060 membrane sold by Sulzer.

According to one embodiment, the process is chosen from the processes of continuous, semi-continuous, or batchwise type.

The present invention more particularly provides a process for producing (meth)acrylic esters having good selectivity, enabling effective elimination of water and enabling the energy cost to be reduced while minimizing the installation cost, which is directly proportional, for a membrane-based process, to the hourly flow rate of permeate per square meter of membrane installed.

Moreover, in the specific case of the use of a hydrophobic membrane, it is possible to treat an aqueous stream containing less than 7% organic compounds and thus to reduce the size of the purification column which will be placed downstream, and hence its energy consumption, or even to dispense with it entirely.

Surprisingly, in relation to the process described in document FR 2 980 475, the steps of treatment by membrane separation according to the invention have very good performance outside the concentration ranges described, and make it possible to treat aqueous streams at higher hourly velocities. These performance levels are linked essentially to the choice of the alcohol and hence of the ester used, especially due to their apolar nature which makes the passage of the water through the hydrophilic membrane easy.

DESCRIPTION OF EMBODIMENTS OF THE INVENTION

Figure 1:
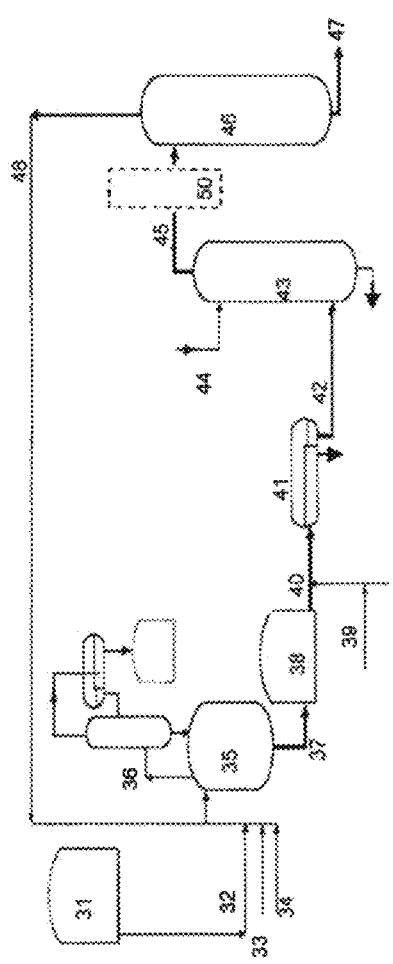
FIG. 1 schematically depicts a facility for carrying out a semi-continuous process for producing (meth)acrylic ester.

The invention is now described in more detail, and nonlimitingly, in the following description.

The terms "(meth)acrylic" and "(meth)acrylate" mean, as is customary, "acrylic or methacrylic" and "acrylate or methacrylate", respectively.

Unless indicated otherwise, the compositions given in percentages are understood as weight values.

The alcohol compound used in the context of the invention may be linear or branched. It may be a primary alcohol or a secondary alcohol. It may comprise 4 or 5 or 6 or 7 or 8 or 9 or 10 carbon atoms. It may be substituted or unsubstituted, and preferably it is unsubstituted. The alcohol compound may especially be butanol, 2-ethylhexanol or 2-octanol.

The corresponding esters obtained are butyl acrylate or butyl methacrylate, 2-ethylhexyl acrylate or 2-ethylhexyl methacrylate, 2-octyl acrylate or 2-octyl methacrylate.

Preferably, the (meth)acrylic acid is acrylic acid.

The reaction for esterification of (meth)acrylic acid with alcohol is carried out in the presence of a catalyst which may be for example an acidic cation exchange resin in the case of heterogeneous catalysis, or, in the case of homogenous catalysis, which may be an inorganic acid of sulfuric acid type, or an organic sulfonic acid such as methanesulfonic acid, para-toluenesulfonic acid, benzenesulfonic acid, dodecylsulfonic acid or mixtures thereof.

Generally speaking, the esterification reaction is carried out in the presence of a stoichiometric excess of alcohol.

The reaction mixture (also referred to hereinafter as the reaction stream) contains the ester produced, and also the unreacted reagents—mainly alcohol—which represent the light compounds to be separated, and if possible recycled, and heavy by-products resulting from side reactions.

According to the invention, the streams undergoing membrane separation dehydration are aqueous streams containing no, or virtually no, heavy by-products, that is to say streams downstream of the treatment for separating by-products having a boiling point higher than that of the (meth)acrylic ester.

According to one embodiment, the stream treated by membrane separation is a stream subjected to the final distillation leading to the recovery of the purified (meth) acrylic ester. According to this embodiment, the aqueous stream consequently contains a high content of (meth) acrylic ester, generally greater than 50%.

According to one embodiment, the stream treated by membrane separation is an aqueous stream generated by settling out the reaction mixture, the organic phase separated by settling out containing virtually no water. According to this embodiment, the aqueous stream contains more than 80% of water and a low content of organic compounds, generally less than 10%.

According to one embodiment, the stream treated by membrane separation is a stream resulting from the distillation of the light by-products present in the reaction mixture. According to this embodiment, the aqueous stream consequently contains a high content of alcohol, generally greater than 20%.

According to the invention, the streams treated by membrane separation may contain water within a wide range, from 0.5 to 99%, alcohol within a concentration range extending from approximately 1 to 60%, ester in a concentration range extending from approximately 0.5 to 70%, and, to a lesser extent, acid in a concentration range which may extend up to 15%.

According to one embodiment, the stream treated by membrane separation comprises from 50 to 70% of (meth) acrylic ester, from 20 to 30% of alcohol, from 0 to 12% of (meth)acrylic acid, and from 3 to 12% of water.

According to one embodiment, the stream treated by membrane separation comprises from 80 to 99% of water, less than 2% of (meth)acrylic ester and from 1 to 20% of alcohol.

According to one embodiment, the stream treated by membrane separation comprises from 0.5 to 15% of (meth) acrylic acid, from 25 to 65% of (meth)acrylic ester, from 20 to 60% of alcohol and from 0.5 to 15% of water.

According to the invention, the step of membrane separation dehydration is carried out by pervaporation (feedstock in liquid phase and vaporization of the permeate on passing through the membrane), or by vapor permeation (feedstock in vapor phase), preferably at a temperature ranging from 50° C. to 100° C., more preferentially from 55° C. to 85° C.

FIG. 1 depicts the embodiment according to which the step of membrane separation is applied to a stream subjected to the final distillation leading to the recovery of the purified (meth)acrylic ester. FIG. 1 corresponds to a semi-continuous process (with batchwise reaction), the facility comprising a single reactor 35. This reactor 35 is supplied by a feed line for alcohol compound 32 (originating from a tank for alcohol compound 31), a feed line for (meth)acrylic acid 33 and a feed line for additive(s) 34, for example a feed line for acid catalyst such as sulfuric acid, and/or polymerization inhibitor.

The reactor 35 is provided with a system for eliminating water 36, comprising a column, a settling tank, a recycling line and a water purge line.

At the outlet of the reactor 35, the reaction stream is recovered by a line for drawing off the reaction stream 37. This line supplies a storage tank 38, at the outlet of which the reaction stream is recovered by a first transfer line 40. A feed line for neutralizing compound 39 is connected to the first transfer line 40 and enables the neutralization of the reaction stream. By way of neutralizing compound, a basic compound such as sodium hydroxide is used.

The first transfer line 40 supplies a settling tank 41 making it possible to purge a portion of the water contained in the reaction stream 40. At the outlet of the settling tank 41, a second transfer line 42 is connected which supplies a washing column 43 provided with a water supply line 44. A third transfer line 45 is connected at the outlet of the washing column 43, which supplies a distillation column 46, after elimination of water by means of a membrane separation dehydration unit 50, arranged on the transfer line 45.

At the bottom of the distillation column 46, a line for drawing off the stream rich in (meth)acrylic ester compound 47 is connected, via which line the essentially purified (meth)acrylic ester compound is recovered.

At the top of the distillation column 46 is connected a line for recycling 48 the stream rich in unreacted reagents, in particular rich in unreacted alcohol compound, via which line a mixture of acid, alcohol compound, (meth)acrylic ester compound and water is recovered. This mixture is returned to the reaction, the line for recycling the stream rich in unreacted alcohol compound being connected at the inlet of the reactor 35, after an optional additional elimination of the water contained in the mixture.

This additional elimination may be carried out by means of a membrane separation dehydration unit (not shown), arranged on the line for recycling the stream rich in unreacted alcohol compound 48.

The membrane separation dehydration unit 50 may be a pervaporation unit (feedstock in liquid phase and vaporization of the permeate on passing through the membrane), or a vapor permeation unit (feedstock in vapor phase).

The dehydration is preferably carried out at a temperature ranging from 50° C. to 100° C., more preferentially from 55° C. to 85° C.

The membranes used are preferably hydrophilic membranes based on polyvinyl alcohol or an inorganic ceramic membrane such as a zeolite.

The mixture which is dehydrated in the membrane separation dehydration unit 50 comprises from 50 to 70% of (meth)acrylic ester, from 20 to 30% of alcohol, from 0 to 12% of (meth)acrylic acid, and from 3 to 12% of water.

The facility represented in FIG. 1 may in particular be used for the semi-continuous production of butyl acrylate from butanol, 2-ethylhexyl acrylate from 2-ethylhexanol, or 2-octyl acrylate from 2-octanol.

Figure 2:
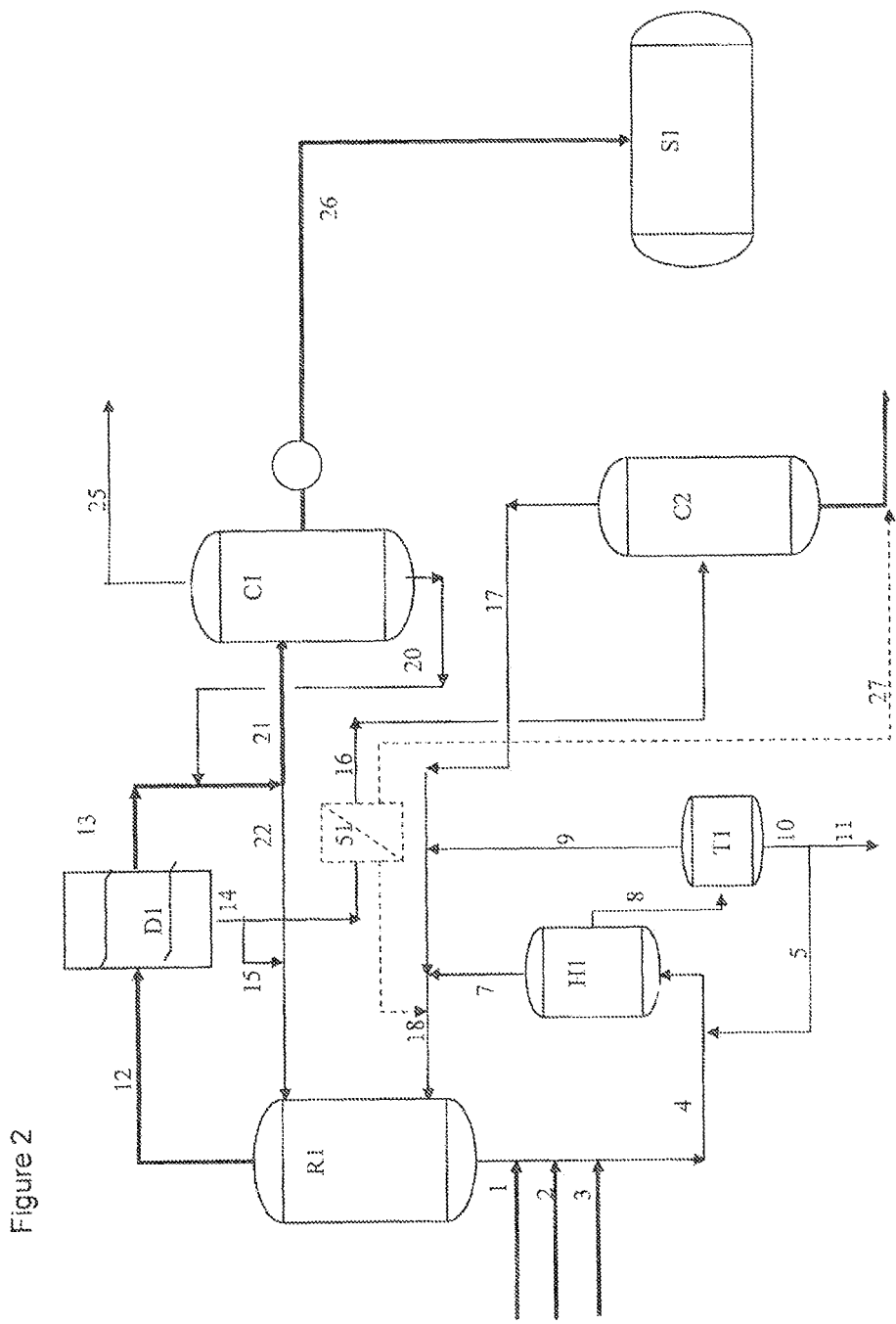
FIG. 2 schematically depicts a facility for carrying out a continuous process for producing (meth)acrylic ester with homogenous catalysis.

FIG. 2 depicts an embodiment according to which the step of membrane separation is applied to the aqueous stream generated by settling out of the reaction mixture.

According to FIG. 2, depicting a continuous process, the facility comprises a single reactor R1. This reactor R1 is supplied by a feed line for alcohol compound 1, a feed line for (meth)acrylic acid 2, and a feed line for additive(s) 3, for example a feed line for catalyst such as sulfuric acid, methanesulfonic acid or para-toluenesulfonic acid.

The reactor R1 is connected to a column (not shown), a settling tank D1, and a recycling line.

At the outlet of the reactor and the column thereof, the tops products are delivered, via line 12, to a settling tank D1.

The organic phase is drawn off via line 13 to be returned either to the reactor via line 22 or to a distillation column C1 via line 21. The final product after distillation in column C1 is sent to storage tank S1 via a lateral drawing-off line 26.

The product from the bottom of column C1 comprising essentially the ester formed and heavy products is recycled to the reaction via line 20, while the light products are delivered to a purge treatment system via line 25.

The aqueous phase from the settling tank D1 is delivered, via line 14, either to the reflux of the reactor column via 15, or to a distillation column C2 via 16. Column C2 makes it possible to recover the organic compounds contained in this aqueous phase and to return them, via line 17, to the reactor.

According to the invention, a membrane separation dehydration unit 51 is placed at the outlet of the settling tank D1 on line 14 for the aqueous phase. It is then possible to deliver the organic phase, contained in this water-rich phase and separated off by said dehydration unit, to the reactor via line 18, and to deliver the aqueous phase containing no organic compounds either to column C2, via line 16, or directly to the water treatment plant as a function of the number of separation stages of the membrane process, via line 27.

The supply of heat to the reactor R1 is ensured by the circulation loop 4 which is heated at the boiler H1 then returned into the reactor via line 7, or delivered to a heat treatment system T1, via line 8, such as a film evaporator or thermal cracker, so as to regenerate a portion of the stream to return it to the reactor via line 9. The treated stream 10 (heavy products) is purged via line 11 or partially recycled via line 5.

The membrane separation dehydration unit 51 may be as described above in relation to FIG. 1, but preferably with a hydrophobic membrane such as the 4060 membrane sold by Sulzer.

In this embodiment, the stream subjected to the membrane separation dehydration 51 is a water-rich stream, comprising from 80 to 99% of water, less than 2% of (meth)acrylic ester and from 1 to 20% of alcohol. The facility depicted in FIG. 2 may in particular be used for the continuous production of butyl acrylate from butanol and acrylic acid with homogenous acid catalysis.

Figure 3:
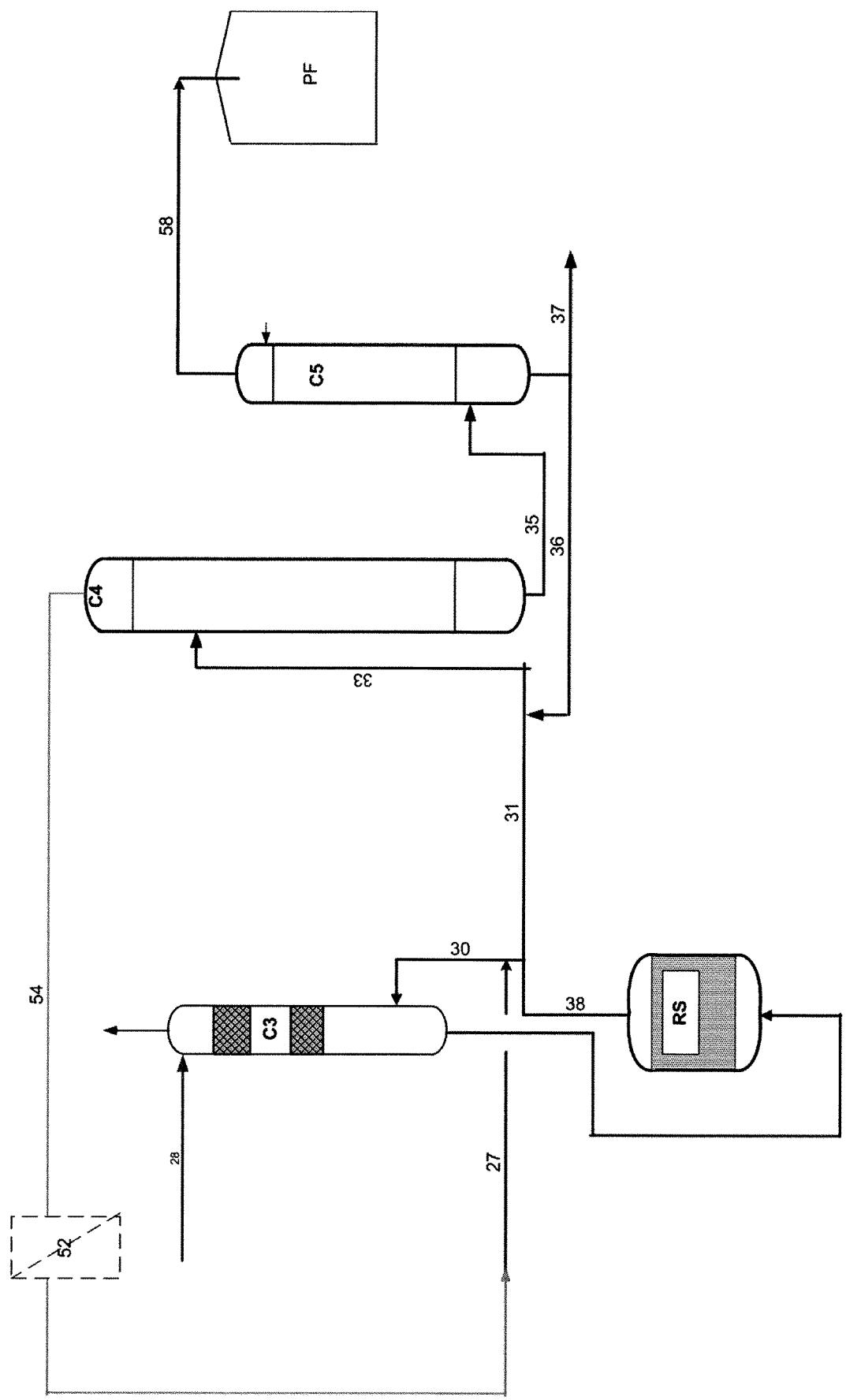
FIG. 3 schematically depicts a facility for carrying out a continuous process for producing (meth)acrylic ester with heterogeneous catalysis.

FIG. 3 depicts an embodiment according to which the step of membrane separation is applied to a stream resulting from the distillation of the light by-products present in the reaction mixture.

With reference to FIG. 3, according to another embodiment of a continuous process, the facility comprises a single reactor RS. This reactor RS contains an acid resin as heterogeneous catalyst. It has a distillation column C3 overhead which makes it possible to eliminate the reaction water toward the wastewater treatment plant. Column C3 is supplied at the top by a stream of cold alcohol 28. The bottom of column C3 is delivered to the reactor RS. The acrylic or methacrylic acid used in the reaction is injected via line 27. The product 30 at the top of the reactor RS returns to the column bottom via line 38, and also a part 31/33 thereof passes to a distillation column C4. The recycled alcohol originating from the top of column C4 via line 54 is delivered to the reactor via line 27.

According to the invention, the stream from the top of column C4 undergoes a step of dehydration in a membrane separation unit 52 which makes it possible to eliminate a large portion of the water contained in the stream before recycling to the reaction. The stream from the bottom of column C4 is delivered, via line 35, to the final tailing column C5 which makes it possible to separate off the heavy by-products at the bottom and the desired ester at the top. The purified ester is delivered into the storage tank PF via line 58. The stream from the bottom of column C5 is either partially recycled 36 to the feed for column C4, or delivered 37 to an effluent treatment plant.

The membrane separation dehydration unit 52 may be as described above in relation to FIG. 1.

According to this embodiment, the stream subjected to the membrane separation dehydration unit 52 comprises from 0.5 to 15% of (meth)acrylic acid, from 25 to 65% of (meth)acrylic ester, from 20 to 60% of alcohol and from 0.5 to 15% of water.

The facility depicted in FIG. 3 may in particular be used for the continuous production of 2-ethylhexyl acrylate from 2-ethylhexanol and acrylic acid with heterogeneous acid catalysis.

The following examples illustrate the present invention without aiming to limit the scope of the invention as defined by the appended claims.

EXAMPLES

Example 1

Tests were carried out on a Sulzer membrane separation pilot having a membrane surface area of 170 cm². The membrane tested is a hydrophilic membrane based on polyvinyl alcohol with the reference Pervap® 1201.

Various streams originating from a real facility for producing butyl acrylate were applied to the membrane. These streams correspond to stream 45 depicted in FIG. 1. The streams mainly comprise butyl acrylate, butanol, water and optionally acrylic acid.

The permeate obtained contains between 95% and 99% water. In other words, the selectivity of the membrane is excellent, and the latter is not substantially affected by the presence of the ester.

As a function of the test conditions and temperatures, the stream passing through the membrane varies from 0.8 kg/m²·h to 2.7 kg/m²·h, which represents high values compared to the values generally achieved in the processes of the prior art.

No degradation of the membrane was observed, despite the presence of acrylic acid and acrylic ester.

The results obtained with the Pervap® 1201 membrane are summarized in table 1.

TABLE 1

|   | T (° C.) | Percentage by weight Feed | | | | P downstream Mbar | Percentage by weight Permeate | | | | Permeate stream J kg/m²·h | Selectivity | |
|---|---|---|---|---|---|---|---|---|---|---|---|---|---|
|   |   | BuOH | BUA | H₂O | AA |   | BuOH | BUA | H₂O | AA |   | $\alpha_{H2O/R}$ | $\beta_{H2O/H2Ol}$ |
| A | 65.0 | 26.9 | 56.4 | 5.5 | 11.1 | 60.0 | 0.7 | 0.2 | 98.4 | 0.6 | 0.8 | 1081 | 18.0 |
|   | 75.0 | 26.9 | 56.4 | 5.5 | 11.1 | 60.0 | 0.6 | 0.1 | 98.1 | 1.1 | 1.3 | 901 | 18.0 |
|   | 80.0 | 26.9 | 56.4 | 5.5 | 11.1 | 60.0 | 0.6 | 0.2 | 98.5 | 0.7 | 1.7 | 1115 | 18.0 |
|   | 90.0 | 26.9 | 56.4 | 5.5 | 11.1 | 60.0 | 0.3 | 0.1 | 99.2 | 0.4 | 1.8 | 2235 | 18.2 |
| B | 62.8 | 30.0 | 66.7 | 3.3 | 0.0 | 60.0 | 4.1 | 0.1 | 95.6 | 0.0 | 0.9 | 638 | 29.3 |
|   | 69.0 | 30.0 | 66.7 | 3.3 | 0.0 | 60.0 | 2.9 | 0.2 | 96.8 | 0.0 | 1.3 | 909 | 29.7 |
|   | 80.0 | 30.0 | 66.7 | 3.3 | 0.0 | 60.0 | 1.9 | 0.2 | 97.9 | 0.0 | 2.0 | 1401 | 30.0 |
|   | 87.2 | 30.0 | 66.7 | 3.3 | 0.0 | 60.0 | 1.4 | 0.1 | 98.5 | 0.0 | 2.7 | 1922 | 30.2 |

The separation factor α is calculated by:

$$\alpha_{H2O/R} = \frac{y_{H2O}/y_R}{x_{H2O}/x_R}$$

where $y_{H2O}$ and $x_{H2O}$ are the fractions by weight of water in the permeate and in the feed, respectively. In the case of pervaporation of the multiconstituent mixtures, $y_R$ and $x_R$ are $(1-y_{H2O})$ and $(1-x_{H2O})$, respectively.

The β factor, or enrichment factor, is the ratio of the concentration of water in the permeate to the concentration of water in the feed.

Example 2

Tests were carried out on a Sulzer membrane separation pilot having a membrane surface area of 170 cm². The membrane tested is a hydrophobic membrane with the reference Pervap® 4060.

A stream originating from a real facility for producing butyl acrylate was applied to the membrane. This stream corresponds to stream 14 depicted in FIG. 2. This stream mainly comprises water (95.2%), with a small amount of butanol (4.7%) and traces of butyl acrylate (0.1%).

The results obtained at different temperatures with the Pervap® 4060 membrane are summarized in table 2.

TABLE 2

| T (° C.) | Percentage by weight Feed | | | P downstream mbar | Percentage by weight Permeate | | | Permeate stream J (kg/m²·h) | Selectivity $\alpha_{H2O/R}$ | Selectivity $\beta_{H2O/H2Ol}$ |
|---|---|---|---|---|---|---|---|---|---|---|
|   | BuOH | BUA | H₂O |   | BuOH | BUA | H₂O |   |   |   |
| 59.75 | 4.7 | 0.1 | 95.2 | 60 | 76.3 | 8.0 | 15.2 | 1.86 | 111 | 17.6 |
| 67.15 | 4.7 | 0.1 | 95.2 | 60 | 76.2 | 8.0 | 15.2 | 3.26 | 111 | 17.6 |
| 78.4 | 4.7 | 0.1 | 95.2 | 60 | 77.3 | 5.4 | 16.0 | 6.06 | 105 | 17.3 |
| 90.65 | 4.7 | 0.1 | 95.2 | 60 | 78.9 | 3.1 | 16.9 | 7.10 | 98 | 17.1 |

The permeate enriched in alcohol may advantageously be recycled to the reaction.

Example 3

Tests were carried out on a Sulzer membrane separation pilot having a membrane surface area of 170 cm². The membrane tested is a hydrophilic membrane based on polyvinyl alcohol with the reference Pervap® 1201.

Two streams originating from a real facility for producing 2-ethylhexyl acrylate (2EHA) from 2-ethylhexanol (2EHeOH) were applied to the membrane at different temperatures. These streams correspond to stream 54 depicted in FIG. 3. The streams comprise alcohol, ester, acid and a small amount of water.

The results obtained with the Pervap® 1201 membrane are summarized in table 3.

TABLE 3

| T (° C.) | Percentage by weight Feed | | | | P downstream | Percentage by weight Permeate | | | | Permeate stream | Selectivity | Selectivity |
|---|---|---|---|---|---|---|---|---|---|---|---|---|
| | 2EHeOH | 2EHA | $H_2O$ | AA | mbar | 2EHeOH | 2EHA | $H_2O$ | AA | J (kg/m$^2$ · h) | $\alpha_{H2O/R}$ | $\beta_{H2O/H2OI}$ |
| 61.6 | 31.9 | 55.5 | 2.2 | 10.1 | 60 | 0.0 | 0.0 | 96.3 | 3.4 | 1.01 | 1134 | 43.5 |
| 69.75 | 31.9 | 55.5 | 2.2 | 10.1 | 60 | 0.0 | 0.0 | 95.1 | 4.6 | 1.46 | 848 | 42.9 |
| 78.8 | 31.9 | 55.5 | 2.2 | 10.1 | 60 | 0.0 | 0.0 | 95.0 | 4.7 | 2.17 | 832 | 42.9 |
| 85.8 | 31.9 | 55.5 | 2.2 | 10.1 | 60 | 0.0 | 0.0 | 95.0 | 4.8 | 2.55 | 830 | 42.9 |
| 60.8 | 52.8 | 32.5 | 2.1 | 12.3 | 60 | 0.1 | 0.0 | 96.3 | 3.3 | 0.79 | 1213 | 45.4 |
| 69.05 | 52.8 | 32.5 | 2.1 | 12.3 | 60 | 0.1 | 0.0 | 95.7 | 4.0 | 1.24 | 1027 | 45.1 |
| 79.95 | 52.8 | 32.5 | 2.1 | 12.3 | 60 | 0.0 | 0.0 | 95.7 | 4.3 | 1.75 | 1015 | 45.0 |
| 87.75 | 52.8 | 32.5 | 2.1 | 12.3 | 60 | 0.1 | 0.0 | 96.4 | 3.3 | 2.12 | 1224 | 45.4 |

The dehydration unit makes it possible to eliminate most of the water present in the stream containing the residual 2-ethylhexanol before it is recycled to the reaction.

The invention claimed is:

1. A process for producing an alkyl (meth)acrylate or alkyl acrylate comprising a linear or branched alkyl chain comprising from 4 to 10 carbon atoms, by direct esterification of (meth)acrylic acid or acrylic acid with a linear or branched alcohol comprising from 4 to 10 carbon atoms in the presence of a catalyst, leading to the formation of a reaction mixture comprising an ester, unreacted acid and alcohol, light by-products and heavy by-products, which mixture is purified by separation to obtain purified alkyl (meth)acrylate or alkyl acrylate, said purification by separation comprising: i) a step of settling out the reaction mixture to produce an aqueous feed stream and an organic stream and ii) a step of treating the aqueous feed stream originating from settling out of the reaction mixture to membrane separation dehydration;
   wherein the feed stream treated by membrane separation comprises from 80 to 99% by weight of water, less than 2% by weight of (meth)acrylic ester or acrylic ester and from 1 to 20% by weight of alcohol,
   wherein said membrane consists of a hydrophobic polymeric membrane,
   wherein said step of membrane separation dehydration is dehydration by pervaporation or vapor permeation at a temperature ranging from 50 to 100° C. and without dephlegmation, and
   wherein a permeate is obtained having a lower water percentage by weight and a higher alcohol percentage by weight than that of the feed stream.

2. The process as claimed in claim 1 wherein the alcohol is selected from the group consisting of butanol, 2-ethylhexanol and 2-octanol.

3. The process as claimed in claim 1 wherein the acid is acrylic acid.

4. The process as claimed in claim 1 which is continuous, semi-continuous, or batch.

* * * * *